United States Patent [19]

Clausen

[11] Patent Number: 5,470,717
[45] Date of Patent: Nov. 28, 1995

[54] METHOD FOR THE PREPARATION OF CERTAIN β-LACTAM ANTIBIOTICS

[75] Inventor: Kim Clausen, Tølløse, Denmark

[73] Assignee: Gist-Brocades N.V., Netherlands

[21] Appl. No.: 240,772

[22] PCT Filed: Dec. 18, 1992

[86] PCT No.: PCT/DK92/00388

§ 371 Date: May 12, 1994

§ 102(e) Date: May 12, 1994

[87] PCT Pub. No.: WO93/12250

PCT Pub. Date: Jun. 24, 1993

[30] Foreign Application Priority Data

Dec. 19, 1991 [EP] European Pat. Off. ............. 91610096
May 14, 1992 [DK] Denmark ................... 0642/92

[51] Int. Cl.$^6$ ............................ C12P 37/04; C12P 35/00; C07D 501/06

[52] U.S. Cl. .................................... 435/47; 435/50
[58] Field of Search ......................... 435/47, 50

[56] References Cited

U.S. PATENT DOCUMENTS

| 4,003,896 | 1/1977 | Faarup | 260/243 |
| 4,256,733 | 3/1981 | Barth | 540/310 |
| 4,677,100 | 6/1987 | Nakagawa et al. | 540/222 |

FOREIGN PATENT DOCUMENTS

| 0339751 | 11/1989 | European Pat. Off. |
| WO92/01061 | 1/1992 | WIPO |

*Primary Examiner*—Herbert J. Lilling
*Attorney, Agent, or Firm*—Bierman and Muserlian

[57] ABSTRACT

The present invention relates to an improved method for the preparation of certain β-lactam antibiotics by enzymatic acylation or by deprotection of a protected intermediate.

11 Claims, No Drawings

5,470,717

METHOD FOR THE PREPARATION OF CERTAIN β-LACTAM ANTIBIOTICS

CROSS-REFERENCE TO RELATED APPLICATIONS

This application is a continuation of PCT/DK92/00388 filed Dec. 18, 1992, the contents of which are incorporated herein by reference.

FIELD OF THE INVENTION

The present invention relates to an improved method for the preparation of cephalosporins, i.e. β-lactam antibiotics comprising a 7-amino-8-oxo-5-thia-1-azabicyclo[4.2.0]oct-2-ene nucleus.

BACKGROUND OF THE INVENTION

The bulk market for β-lactam antibiotics is a highly competitive field and one of the parameters which influence the price is the purity of the product. Therefore, it is very important for a producer to have access to a production method which gives a high yield of a very pure product.

Presently, most of the cephalosporins used are so-called semi-synthetic products. This designation implies that they are obtained by modifying a β-lactam product obtained by fermentation by one or more chemical reactions. Typically, one of the chemical reactions involved in this modification is acylation of the 7-amino group of an intermediate cephalosporin nucleus the parent of which is originally obtained by fermentation and optionally further modified in other chemical reactions.

In the following, the acyl group introduced at the 7-amino group is referred to as the cephalosporin side chain or just the side chain. The acid corresponding to the side chain is designated the side chain acid. The designation "a cephalosporin nucleus" designates a compound the acylation of which with the cephalosporin side chain results in the formation of a β-lactam antibiotic or, more specifically, a cephalosporin.

The acylation can be performed by reacting an optionally protected form of the cephalosporin nucleus with a derivative—e.g. the acid chloride—of an optionally protected form of the cephalosporin side chain in an organic solvent—typically methylene chloride—in the presence of a base. As an alternative to the acid chloride a mixed anhydride can be used for the acylation. In both cases, the acylation has to be carried out under anhydrous conditions at a temperature which should preferably be below zero.

The acylation reaction never comes to completion and at the point when the work up is started, the reaction mixture will contain the desired product as well as unreacted starting materials and possible byproducts. After the acylation, the protective groups, if any, have to be removed either in situ or after the protected intermediate product has been isolated. The working up of the intermediate product and the removal of the protective groups generally involves at least one step in which the product is contacted with water or an aqueous solvent. During the deprotection operation great care must be taken to avoid cleavage of the acyl bond just established.

The final purification of β-lactam antibiotics can be hampered by the fact that the acid-base properties and the solubility of some of the impurities contained in the crude products are not very much different from the similar properties of the desired product. This implies that co-precipitation of impurities may easily take place when the crude product is reprecipitated or recrystallized and it can therefore be difficult to achieve a high purity of the product and a high yield at the same time.

As an alternative to the methods outlined above, the side chain can be introduced by an enzyme catalyzed acylation. In this case either the free acid corresponding to the side chain or an activated derivative thereof such as the amide or a lower alkyl ester can be utilized as the source of the acyl group. The enzymatic acylation can be carried out at ambient temperature and thus, the expense and the inconvenience connected with working at low temperature is eliminated. The solvent is water or a mixture of water with water-miscible organic solvents. The stability of the desired products and the rate of the acylation reaction both depend on the pH value in the reaction mixture. Thus, at a pH value of about 4, the desired products are fairly stable and the rate of the acylation reaction is fairly low. At a pH value of about 7, deacylation of the desired product progresses and at the same time the rate of the acylation reaction is high. This means that the pH value at which the enzymatic acylation is most favourably carried out under ordinary conditions constitutes a compromise between these oppositely directed preferences.

A method for the purification of cephalexin is described in U.S. Pat. No. 4,003,896 (to NOVO INDUSTRI A/S). According to this patent, naphthalene or a naphthalene derivative is added to an aqueous solution containing crude cephalexin to provide a sparingly soluble complex of naphthalene or of the naphthalene derivative with cephalexin. This complex is isolated and decomposed to provide a high yield of very pure cephalexin. However excellent the purification method described works, it can not but secure a good yield of the purification step.

SUMMARY OF THE INVENTION

Surprisingly, it has now been found that a very high yield of a complex of a cephalosporin with naphthalene or a naphthalene derivative can be obtained in situ in a very fast reaction, when the corresponding cephalosporin nucleus is acylated enzymatically in water or in an aqueous solvent in the presence of naphthalene or a naphthalene derivative and with the acid corresponding to the cephalosporin side chain or a derivative thereof, e.g. the amide or a lower alkyl ester thereof as the acylating agent. The complex produced is sparingly soluble in water and in aqueous media containing water-miscible organic solvents. The cephalosporin bound in the sparingly soluble complex is not susceptible to hydrolysis and therefore, the pH value in the reaction mixture can be optimized to ensure the highest possible rate of the acylation reaction without risking undesired hydrolysis or deacylation of the desired product. After completion of the enzymatic reaction, the complex can be isolated and decomposed by methods known per se to give a very high yield of an excellently pure cephalosporin.

Also when the protective groups of a cephalosporin intermediate are to be removed by hydrolysis, e.g. after the introduction of the side chain via a non-enzymatic acylation, the hydrolysis can advantageously be carried out in the presence of an excess of naphthalene or a naphthalene derivative. When the hydrolysis is completed the complex formed can be isolated and further processed as mentioned above.

Thus, the present invention relates to a method for preparing a cephalosporin comprising adding naphthalene or a naphthalene derivative to the reaction mixture in which the cephalosporin is produced followed by isolation by methods known per se of the cephalosporin from the sparingly soluble complex formed.

In a first preferred embodiment of the invention, the reaction mixture to which naphthalene or a naphthalene derivative is added is a reaction mixture in which the cephalosporin is formed by acylation of the 7-amino group of a cephalosporin nucleus which is a substituted 7-amino-8-oxo-5-thia-1-azabicyclo[4.2.0]oct-2-ene with a cephalosporin side chain acid or acid derivative under the influence of an enzyme.

In a further preferred embodiment of the invention, the cephalosporin nucleus which is acylated is 7-aminocephalosporanic acid.

In a further preferred embodiment of the invention, the cephalosporin nucleus which is acylated is 7-amino-7-methoxycephalosporanic acid.

In a further preferred embodiment of the invention, the cephalosporin nucleus which is acylated is 7-aminodesacetoxycephalosporanic acid.

In a further preferred embodiment of the invention, the cephalosporin nucleus which is acylated is 3-chloro-7-amino-3-cephem-4-carboxylic acid.

In a further preferred embodiment of the invention, the cephalosporin side chain used as an acylating agent is D-phenylglycine.

In a further preferred embodiment of the invention, the cephalosporin side chain used as an acylating agent is D-phenylglycine amide.

In a further preferred embodiment of the invention, the cephalosporin side chain used as an acylating agent is D-phenylglycine methylester.

In a further preferred embodiment of the invention, the cephalosporin side chain used as an acylating agent is the ethyl ester, the propyl ester or the isopropyl ester of D-phenylglycine.

In a further preferred embodiment of the invention, the cephalosporin side chain used as an acylating agent is D-4-hydroxyphenylglycine.

In a further preferred embodiment of the invention, the cephalosporin side chain used as an acylating agent is D-4-hydroxyphenylglycine amide.

In a further preferred embodiment of the invention, the cephalosporin side chain used as an acylating agent is D-4-hydroxyphenylglycine methylester.

In a further preferred embodiment of the invention, the cephalosporin side chain used as an acylating agent is the ethylester, the propylester or the isopropylester of D-4-hydroxyphenylglycine.

In a further preferred embodiment of the invention, the cephalosporin side chain used as an acylating agent is 2-amino-2-phenylpropionic acid.

In a further preferred embodiment of the invention, the cephalosporin side chain used as an acylating agent is 2-amino-2-phenylpropionamide.

In a further preferred embodiment of the invention, the cephalosporin side chain used as an acylating agent is 2-amino-2-phenylpropionic acid methylester.

In a further preferred embodiment of the invention, the cephalosporin side chain used as an acylating agent is the ethylester, the propylester or the isopropylester of 2-amino-2-phenylpropionic acid.

In a further preferred embodiment of the invention, the cephalosporin nucleus is acylated under the influence of an enzyme which can be classified as a penicillin acylase or as an ampicillin hydrolase.

In a further preferred embodiment of the invention, the cephalosporin nucleus is acylated under the influence of an enzyme from *Escherichia coli, Acetobacter pasteurianus, Xanthomonas citrii, Kluyvera citrophila, Bacillus megaterium* or *Pseudomonas melanogenum.*

In a further preferred embodiment of the invention, the cephalosporin nucleus is acylated under the influence of an immobilized enzyme.

In a further preferred embodiment of the invention the cephalosporin nucleus is acylated under the influence of an immobilized enzyme, and after the reaction the particles carrying the enzyme are separated from the remainder of the reaction mixture which comprises the particulate solid complex between the β-lactam antibiotic formed and naphthalene or a naphthalene derivative and optionally one or more other particulate solid component(s) and a liquid by giving the β-lactam antibiotic complex and the other particulate solid component(s), if any, a particle size which is different from the size of the particles carrying the enzyme and filtering or centrifuging the reaction mixture using equipment which will retain the component having the larger particles, be it the particles carrying the immobilized enzyme or the other solid component(s), and let the remainder of the mixture pass through.

In a further preferred embodiment of the invention the cephalosporin nucleus is acylated under the influence of an enzyme and after the reaction the particles carrying the enzyme are separated from the remainder of the reaction mixture which comprises the particulate solid complex between the β-lactam antibiotic formed and naphthalene or a naphthalene derivative and optionally one or more other particulate solid component(s) and a liquid by giving the βlactam antibiotic complex and the other particulate solid lo component(s), if any, a particle size which is smaller than the size of the particles carrying the enzyme and filtering or centrifuging the reaction mixture using equipment which will retain the particles carrying the immobilized enzyme and let the remainder of the mixture pass through.

In a further preferred embodiment of the invention, the cephalosporin is formed by deprotection of a protected intermediate.

In a further preferred embodiment of the invention, the formation of the β-lactam antibiotic takes place with water as the only solvent.

In a further preferred embodiment of the invention, the formation of the β-lactam antibiotic takes place in a medium which is a mixture of water and one or more water-miscible solvents.

In a further preferred embodiment of the invention, the pH value of the reaction mixture is kept in the range from about 2.5 to about 9, preferably in the range from about 4 to about 8, with the proviso that when the cephalosporin is prepared by in situ acylation of a cephalosporin nucleus with the free side chain acid as the acylating agent then the pH value is preferably in the range from about 4 to about 9.

In a further preferred embodiment of the invention, the naphthalene derivative used has the formula:

Naphthyl-R wherein Naphthyl- designates 1-naphthyl or 2-naphthyl and R designates halogen, hydroxy, nitro, cyano, a branched or an unbranched alkyl group, preferably with 1 to 6 carbon atoms e.g. methyl, ethyl, propyl, isopropyl, butyl, isobutyl, sec-butyl or tert-butyl, optionally substituted with a cyano group to provide e.g. a cyano methyl group or a 2-cyano ethyl group, a branched or an unbranched alkoxy group, preferably with 1 to 6 carbon atoms, e.g. methoxy, ethoxy, propoxy, isopropoxy, butoxy, isobutoxy, sec-butoxy or tert-butoxy or an alkanoyl group, preferably with 1 to 6 carbon atoms, e.g. a formyl group, an acetyl group or a propanoyl group.

In a further preferred embodiment of the invention, 2-naphthol is used.

In a further preferred embodiment of the invention, the ratio on a molar basis between 2-naphthol and cephalexin in the reaction mixture in which the cephalosporin is formed is at least 0.45.

In a further preferred embodiment of the invention, part of the naphthalene or naphthalene derivative in the reaction mixture is in solid form.

The advantages of the present invention are, inter alia, the following:

1) The number of steps in the process is reduced as compared to the prior art. This inherently saves time and expenses.
2) The acylation can be carried out at a very high rate. This allows a higher throughput with the same equipment and thus, contributes to a favourable economy of the process.
3) The acylation can be carried out with a high concentration of the reactants. This allows a higher throughput with the same equipment and thus, contributes to a favourable economy of the process.
4) The yield of the acylation is almost quantitative. This facilitates the purification and thus, contributes to a favourable economy of the process.
5) Degradation of the desired product (e.g. deacylation of the 7-amino group or ring opening of the β-lactam ring) is suppressed. This facilitates the purification of the desired product and thus, ensures a better yield.
6) When the acylating agent is the amide or an ester of the side chain acid, the high rate of the acylation reaction ensures a favourable ratio between the desired acylation reaction and the undesired side reaction which leads to hydrolysis of the acylating agent. Hereby an efficient utilization of the costly acylating agent is ensured and the possibility that unreacted acylating agent can be recycled exists.
7) When the acylating agent is the amide or an ester of the side chain acid, the moderate extent of the hydrolysis implies that the content of the free side chain acid in the reaction mixture is low. This facilitates purification.
8) The desired product can be produced without using halogenated solvents (e.g. methylene chloride) in the acylation or deprotection step and in the subsequent working up of the product. This is an advantage, because the residual amount of halogenated solvents accepted by some health authorities is so low that the demand can be quite difficult to meet, if halogenated solvents have been used in the process.

DETAILED DESCRIPTION OF THE INVENTION

Examples of cephalosporins that can be produced by the process of the present invention are cephalexin, cefadroxil, cefaclor, cephaloglycin, cefatrizine, cephalothin and cefaparol.

When a semi-synthetic cephalosporin is produced by non-enzymatic acylation of a cephalosporin nucleus, it will in some cases be necessary to introduce protective groups in the cephalosporin nucleus and sometimes also in the acylating agent, before the acylation can be carried out. After the acylation reaction, the protective groups must be removed. This can be done by selectively hydrolysing the protective groups in water or in an aqueous solvent, but great caution is needed to avoid hydrolysis of the cephalosporin side chain. However, when naphthalene or a naphthalene derivative as specified is present during the hydrolysis, the desired cephalosporin is precipitated in the form of the sparingly soluble complex with naphthalene or the naphthalene derivative immediately when the cephalosporin is produced from the intermediate.

The cephalosporin nuclei as well as the side chain acid or acid derivatives to be used as starting materials in the method according to the present invention are commercially available or can be obtained by methods known per se.

When cephalosporins are produced by enzymatic acylation of a cephalosporin nucleus, the acylating agent can be D-phenylglycine, D-4-hydroxyphenylglycine or the free acid corresponding to another cephalosporin side chain or it can be a derivative of the acid corresponding to the desired side chain such as the amide or a lower alkyl ester thereof. The amide and the esters are preferred. The acylating agent may be used in the form of a salt, for example, the hydrochloride or the sulfate. When a derivative of the acid is used as acylating agent, a problem with the prior art is that the desired acylation competes with hydrolysis of the acylating agent and of the desired product. Thus, acylating agent is wasted and purification of the desired product is hampered. In the process according to the present invention, hydrolysis of the desired product is prevented and therefore, a more effective utilization of the acylating agent is ensured.

The solubility of the acylating agent such as the D-phenylglycine or D-4-hydroxyphenylglycine derivative will vary with the identity of the derivative and with the composition of the reaction medium. In an aqueous system, the solubility of the hydrochloride salt of D-phenylglycine amide is typically approximately 400 mM in the pH range 2–7. However, the solubility is very dependent on the salt components in the solution, as well as on the pH value and the temperature of the solution. Because the reaction mixture contains undissolved naphthalene or naphthalene derivative and by and by also the sparingly soluble complex thereof with the cephalosporin produced, the reaction mixture will usually appear as a slurry. Initially, the reaction mixture may also contain undissolved acylating agent and/or cephalosporin nucleus which will dissolve fully or partially during the course of the reaction.

The enzyme to be used in the process of this invention may be any enzyme catalyzing the reaction in question. Such enzymes have been known since around 1966. Enzymes to be used are, for example, termed penicillin amidases or penicillin acylases and classified as E.C. 3.5.1.11. A number of microbial enzymes are known to have this activity, derived from for example Acetobacter, Xanthomonas, Mycoplana, Protaminobacter, Aeromonas (West German patent application No. 2,163,792) Pseudomonas (Austrian Patent No. 243986), Flavobacterium (Dutch patent application No. 70–09138), Aphanocladium, Cephalosporium (West German patent application No. 2,621,618), *Acetobacter pasteurianus, Bacillus megaterium, Xanthomonas citrii* (European patent application No. 339,751), *Kluyvera citrophila* (Agr. Biol.Chem. 37 (1973), 2797–2804) and *Escherichia coli* (West German patent application No.

2,930,794). The *Escherichia coli* enzyme is commercially available. The enzyme may also be a so-called ampicillin hydrolase, acylase or amidase. In this connection, reference is, inter alia, made to Hakko to Kogyo 38 (1980), 216 et seq., the content of which is incorporated by reference.

In commercial processes involving the use of a catalyst e.g. an enzyme, the price of the catalyst is often a very important parameter in the overall economy of the process. In such cases it is an advantage of major importance if the catalyst can be reused without significant loss of catalytic activity. Thus, although a dissolved enzyme can be used in the method according to the present invention, it is in most cases advantageous to have the enzyme in a reuseable form, for example, in entrapped or immobilized form. Such enzymes can be obtained by methods known in the art. Immobilized *Escherichia coli* enzyme is commercially available, e.g. from Boehringer Mannheim GmbH, Germany, under the trade name Enzygel.

When the catalyst is the only solid component present in a reaction mixture after a reaction mediated by a particulate solid catalyst (e.g. an immobilized enzyme) it can simply be separated by filtration or decantation.

However, after a reaction mediated by a particulate solid catalyst, the reaction mixture may in some cases contain other solid components than the catalyst e.g. the desired product, optional by-products or unreacted solid starting material. In this case the catalyst can sometimes be separated by extraction with organic solvents and/or with acids or bases which will dissolve the solids except for the catalyst. However, the activity of catalysts, including enzymes, is very sensitive to the presence of so-called catalyst poisons. Catalyst poisons exert their activity e.g. by binding very strongly to the catalyst or by decomposing it. Thus, strong acids and bases often have an adverse effect on the activity of catalysts and particularly enzymes generally suffer irreversible damage on exposure to high concentrations of acids or bases. This imposes certain limitations on the use of acids and bases in the work up of reaction mixtures from enzymatic reactions when the enzyme is to be recycled without significant loss of activity. Other limitations on the work up conditions may of course be imposed by the nature of the desired product which may itself be a labile compound.

When an immobilized enzyme is used in the method according to the present invention, an acid or a base cannot be used for dissolving the solid component(s) of the reaction mixture except for the catalyst in the step in which the complex between the desired β-lactam antibiotic and naphthalene or a naphthalene derivative is separated from the enzyme by filtration as this would lead to an unwanted decomposition of the complex. At the same time the enzyme would, depending on the conditions, e.g. the pH value, the temperature and the duration of the process, be partially or completely inactivated. Also, the desired β-lactam antibiotic might suffer decomposition to some extent, again depending i.a. on the pH value, the temperature and the duration of the process. Finally, naphthalene is not soluble in acid or base and this is also the case with many naphthalene derivatives.

As an alternative to dissolving the solid component(s) of the reaction mixture after the reaction except for the solid catalyst and separating the catalyst by filtration, the catalyst can also, according to the present invention, be separated by sieving or filtering the reaction mixture after the reaction or, optionally, in a continous way. In a particularly preferred mode of this embodiment catalyst particles of a well defined size are used and the other solid component(s) of the reaction mixture (e.g. the naphthalene or naphthalene derivative) is (are) given a particle size smaller than that of the catalyst. The separation of the catalyst is then carried out by pouring or pumping the slurry which constitutes the reaction mixture onto a sieve or a filter which will retain the catalyst particles and let the remainder of the mixture pass through. As the skilled person will know, there are several possibilities to influence the size and the shape of the particles to be separated from the catalyst. Thus, when the particles are crystals, which will most frequently be the case, vigorous stirring of the reaction mixture during their formation tends to result in smaller crystals than moderate stirring. Other parameters which influence the crystal growth are: choice of solvent or solvent mixture, temperature, temperature gradient, seeding and ageing of the crystals in the solvent. The separation may be facilitated if the filter plate or sieve is vibrated during the separation dr if the slurry on the filter plate is stirred, preferably with a low shear stirrer. After separation of the catalyst, the reaction mixture can be filtered on a filter which will retain the remaining solid component(s). The filtrate and the filter cake can be worked up separately, some components optionally being recirculated in the process together with the catalyst.

In a further preferred embodiment the method of the invention can be used for producing a cephalosporin in a continuous manner. Thus, a two-tank system can be utilized in which an immobilized enzyme is loaded in tank 1 which is equipped with a sieve at the bottom which will retain the immobilized enzyme and let the remainder of the reaction mixture pass through, and micronized 2-naphthol is loaded in tank 2 which is equipped with a filter at the bottom which will retain the solid material present in tank 2 and let the mother liquor pass through. The two tanks are connected in such a manner that the effluent from the bottom of tank 1 is pumped to the top of tank 2. A filtering or centrifuge unit may optionally be inserted in the flow line from tank 1 to tank 2. The effluent from tile bottom of tank 2 is pumped to the top of tank 1. Also, a filtering or centrifuge unit may optionally be inserted in the flow line from tank 2 to tank 1. Both tanks may be equipped with stirring equipment. The starting materials are initially loaded in tank 1 and by and by as the product is withdrawn supplementary amounts of starting materials may be added to tank 1 continously or at suitable intervals.

The process of this invention is generally carried out in water. Optionally, organic solvents can be added. Organic solvents are preferably selected among watermiscible solvents such as methanol, ethanol, 1-propanol, 2-propanol, 1-butanol, 1,4-butanediol, acetone, acetonitrile, N,N-dimethylformamide and dimethylsulfoxide. In the present specification, the designation "solvent" or "medium" shall not be construed as comprising the reactants.

The process can be carried out at ambient temperature. When the sparingly soluble complex is formed in connection with an enzymatic synthesis of the cephalosporin, the preferred temperature usually is the optimum temperature of the enzyme reaction. The lower limit of the temperature range in which the process can be carried out is determined by the freezing point of the aqueous solvent, whereas the upper limit when an enzyme is involved is determined by the temperature which will inactivate the enzyme.

If an excess of solid naphthalene or naphthalene derivative is present in the reaction mixture, this will be isolated together with the precipitated complex and separated from the cephalosporin by extraction or filtration, when the complex has been decomposed.

Complexes which are sparingly soluble in water can be formed with cephalosporins and a broad range of naphthalene derivatives including naphthalene itself. Besides being sparingly soluble in water, the complexes are also sparingly soluble in organic solvents such as methanol, ethanol, butanol, acetone, ethyl acetate and butyl acetate. When the process is carried out in such a way that initially the major part of the naphthalene derivative is present in solid form, it should preferably be in the form of a fine powder. After the sparingly soluble complex has been isolated and worked up, the naphthalene derivative can be recycled. No adverse effect of the naphthalene or its derivatives on the enzyme activity has been observed.

The present invention is further illustrated by examples which, however, are not to be construed as limiting the scope of protection. The features disclosed in the foregoing description and in the following examples and claims may, both seperately and in any combination thereof, be material for realising the invention in diverse forms thereof.

DEFINITIONS AND METHODS OF ANALYSIS

Abbreviations

7-ACA is 7-aminocephalosporanic acid, 7-ADCA is 7-aminodesacetoxycephalosporanic acid, Cex is cephalexin, D-PG is D-phenylglycine, D-PGA is D-phenylglycine amide and D-PGM is D-phenylglycine methylester, cedrox is cefadroxil, D-HPGA is D-4-hydroxyphenylglycine amide, and D-HPG is D-4-hydroxyphenylglycine.

Enzyme Activity

As definition of penicillin G acylase activity the following is used: one unit (U) corresponds to the amount of enzyme that hydrolyses per minute 1 µmole of penicillin G under standard conditions (5% penicillin G, 0.2M sodium phosphate buffer, pH value 8.0, 28° C.).

HPLC Analysis of Reaction Components

Column: $C_{18}$, YMC 120 Å, 5 µm (4.6×250 mm)
Elution with mixtures of eluents A and B according to Table 1.
Eluent A: 25 mM sodium phosphate buffer, pH 6.5
Eluent B: Acetonitrile

TABLE 1

| Time, minutes | Eluent B, % |
|---|---|
| 0→5 | 1 |
| 5→15 | 1→20 |
| 15→20 | 20→50 |
| 20→25 | 50 |
| 25→27 | 50→1 |
| 27→40 | 1 |

Flow: 1.0 ml/min.
Detection: UV at 215 nm

Retention time in minutes:

| D-PG | 4.36 |
|---|---|
| 7-ADCA | 7.51 |
| D-PGA | 14.37 |
| Cex | 19.14 |
| 2-naphthol | 27.17 |
| D-HPG | 2.60 |
| D-HPGA | 3.70 |
| Cedrox | 20.20 |

EXAMPLE 1

Enzymatic Synthesis of Cephalexin in the Presence of 2-Naphthol

Experiments A–D were performed at room temperature.

Experiment A (Reference)

D-PGA.½$H_2SO_4$ (15 mmol) and 7-ADCA (4 mmol) was dissolved in water. Immobilized enzyme (4 g, Eupergit PCA, 100 U/g (wet), available from Röhm-Pharma) was added and the total volume of the reaction mixture was made up to 20 ml with water after the pH value had been adjusted to 6.4. Representative samples of the reaction mixture including solid constituents (except for the enzyme) were taken after 0, 1, 2, 3, 4 and 5 hours and analysed by HPLC. The results obtained are reported in Table 2.

TABLE 2

| Time | Concentration (mmol/l) found by HPLC | | | |
|---|---|---|---|---|
| (hours) | D-PGA | 7-ADCA | Cex | D-PG |
| 0 | 755 | 196 | — | — |
| 1 | 605 | 121 | 78.9 | 64.7 |
| 2 | 550 | 95.0 | 102.4 | 92.4 |
| 3 | 504 | 86.2 | 112.8 | 131 |
| 4 | 460 | 64.3 | 135 | 151 |
| 5 | 420 | 43.1 | 155 | 165 |

Experiment B

Same conditions as in Experiment A were employed, except that finely ground 2-naphthol (3 mmol) was added to the reaction mixture at the beginning of the experiment. The sparingly soluble complex of cephalexin with 2-naphthol has the approximate composition Cex.2-naphthol$_{1/2}$ and the amount of 2-naphthol added is thus approximately 50% in excess of the amount theoretically necessary for complex formation with all the cephalexin that can possibly be formed in the reaction. Representative samples of the reaction mixture including solid constituents (except for the enzyme) were taken after 0, 1, 2, 3, 4 and 5 hours and analysed by HPLC. The results are reported in Table 3.

TABLE 3

| Time | Concentration (mmol/l) found by HPLC | | | |
|---|---|---|---|---|
| (hours) | D-PGA | 7-ADCA | Cex | D-PG |
| 0 | 748 | 198 | — | — |
| 1 | 630 | 116 | 89.3 | 28.0 |
| 2 | 571 | 70.7 | 130 | 49.4 |
| 3 | 514 | 28.3 | 168 | 64.7 |
| 4 | 460 | 4.1 | 193 | 92.0 |
| 5 | 428 | 3.0 | 195 | 119 |

Experiment C

Same conditions as in Experiment B were employed, except that the reaction was run at pH 6.7. Representative samples of the reaction mixture including solid constituents (except for the enzyme) were taken after 0, 1, 2, 3 and 4 hours and analysed by HPLC. The results obtained are reported in Table 4.

TABLE 4

| Time | Concentration (mmol/l) found by HPLC | | | |
|---|---|---|---|---|
| (hours) | D-PGA | 7-ADCA | Cex | D-PG |
| 0 | 756 | 198 | — | — |
| 1 | 615 | 100 | 98.4 | 32.1 |
| 2 | 513 | 13.3 | 182 | 55.7 |
| 3 | 448 | 2.1 | 196 | 104 |
| 4 | 413 | 2.2 | 197 | 142 |

Experiment D

Same conditions as in Experiment B were employed, except that the reaction was run at pH 7.0. Representative samples of the reaction mixture including solid constituents (except for the enzyme) were taken after 0, 1, 2, 3 and 4 hours and analysed by HPLC. The results obtained are reported in Table 5.

TABLE 5

| Time | Concentration (mmol/l) found by HPLC | | | |
|---|---|---|---|---|
| (hours) | D-PGA | 7-ADCA | Cex | D-PG |
| 0 | 755 | 196 | — | — |
| 1 | 518 | 13.9 | 184 | 44.5 |
| 2 | 444 | 3.1 | 195 | 111 |
| 3 | 370 | 2.1 | 197 | 179 |
| 4 | 315 | 1.9 | 197 | 234 |

The yields of Cex and the ratios between the amount of Cex formed and the amount of D-PG formed due to an undesired side reaction in Experiment A, B, C and D after 5, 4, 2 and 1 hours, respectively, are summarized in Table 6. The figures indicate that the rate at which Cex is formed and the efficiency with which the acylating agent, D-PGA, is utilized are both strongly dependent on the reaction conditions. It should be noted that the yields reported in Table 6 are not the optimal yields.

TABLE 6

| Experiment | A | B | C | D |
|---|---|---|---|---|
| Time (hours) | 5 | 4 | 2 | 1 |
| Yield, Cex | ~78% | >95% | >90% | >90% |
| Cex formed / D-PG formed | 0.94 | 2.08 | 3.23 | 4.17 |

EXAMPLE 2

Enzymatic Synthesis of Cephalexin in the Presence of 2-Naphthol and Subsequent Isolation of the Product The pH value of a mixture of D-PGA.½$H_2SO_4$ (74.7 g, 0.375 mol), 7-ADCA (21.4 g, 0.10 mol) and 2-naphthol (10.8 g, 0.075 mol) in approximately 400 ml of water was adjusted to 6.71 by addition of 4M ammonium hydroxide. Water was added to 450 ml followed by soluble E. coli Pen G acylase (50 ml, approximately 345 U/ml, obtained from Gesellschaft für Biotechnologische Forschung, Braunschweig, Germany) and the mixture was stirred at 25° C.

After 3 hours, the reaction mixture was filtered on a sintered glass filter. The solid residue was washed with butyl acetate (200 ml) and then suspended in a mixture of water (150 ml) and butyl acetate (150 ml). The pH value of the suspension was adjusted to 1.5 by addition of 3M sulfuric acid and stirring was continued for 10 minutes. The water phase was then separated from the butyl acetate phase and washed with further butyl acetate (2×20 ml). The volume of the water phase was reduced to 75 ml by evaporation, 2-propanol (75 ml) was added and the pH value was adjusted to 4.7 by addition of 4M ammonium hydroxide. The slurry obtained was cooled to 5° C. for 15 minutes, whereupon the solid material was collected on a sintered glass filter and washed with water/2-propanol (1:1, 25 ml). After drying in a vacuum oven at 30° C. for 12 hours, 33.8 g (92.5% of the theoretical yield) of cephalexin monohydrate was obtained as a white powder (purity by HPLC: 99.8%).

EXAMPLE 3

Enzymatic Synthesis of Cephalexin in the Presence of 2-Naphthol using an Immobilized Enzyme which can be Recycled E. coli having Penicillin G acylase activity was fermented according to Gebauer, A. et al. *Bioprocess Engineering* 2 (1987) 55–58. Immobilization was performed according to Wümpelmann, M. et al. U.S. Pat. No. 4,892,825 (to Novo Industri A/S). The substance containing the immobilized enzyme was extruded and dried until the residual water content was approximately 10% (w/w). The dried material was milled and a fraction having a particle size distribution of 100–200 µm was obtained from the milled product by the use of appropriate sieves. The enzyme activity in this fraction was found to be approximately 200 Penicillin G acylase Units/g. After swelling in water, the particle size distribution was approximately 200–500 µm.

The pH value of a mixture (slurry) of D-PGA.½$H_2SO_4$ (74.7 g, 0.375 mol), 7-ADCA (21.4 g, 0.10 mol), and 2-naphthol (10.8 g, 0.075 mol, particle size <100 µm) in approximately 300 ml of water was adjusted to 6.7 by addition of 4M ammonium hydroxide. Water was added to 400 ml followed by immobilized E. coli Penicillin G acylase prepared as described above (50 g on dry basis suspended in water to a total of 100 ml), and the mixture was stirred at 25° C.

After 3 hours, the reaction mixture was poured on to a 100 µm pore screen, which retained the particles carrying the enzyme while the remaining part of the reaction mixture, still a slurry, passed through. The slurry passing the screen was filtered on a sintered glass filter which retained the solid material and some of the mother liquor was used to wash the solid material remaining on the 100 µm screen in order to free the enzyme particles from any adhering fine slurry containing the synthesized product. Also the washings were filtered through the sintered glass filter. The product collected on the glass filter was washed with butyl acetate (200 ml) and then suspended in a mixture of water (150 ml) and butyl acetate (150 ml). The pH value of the water phase was adjusted to 1.5 by addition of 3M sulfuric acid and stirring was continued for 10 minutes. The water phase was then separated from the butyl acetate phase and washed with further butyl acetate (2×20 ml). The volume of the water phase was reduced to 75 ml by evaporation, 2-propanol (75 ml) was added and the pH value was adjusted to 4.7 by addition of 4M ammonium hydroxide. The slurry obtained was cooled to 5° C. for 15 minutes, whereupon the solid material was collected on a sintered glass filter and washed with water/2-propanol (1:1, 25 ml). After drying in a vacuum oven at 30° C. for 12 hours, 33.6 g (92.4% of the theoretical yield) of cephalexin monohydrate was obtained as a white powder (purity by HPLC: 99.9%).

After use, the enzyme particles left on the 100 μm screen were washed with water (3×100ml), drained, and finally dried to a water content of approximately 10%. The weight was approximately 49.5 g, and the enzyme activity was found to be approximately 198 Penicillin G acylase Units/g, indicating that practically no loss of activity had occurred. Thus, the immobilized enzyme was suitable for recycling, e.g. in a process as described above.

EXAMPLE 4

Enzymatic Synthesis of Cefadroxil in the Presence of 2-Naphthol

Experiments A and B were performed at 25° C.

Experiment A (Reference)

D-HPGA (130 mmol) and 7-ADCA (40 mmol) was dissolved in water. Immobilized enzyme (50 g, Eupergit PCA, 100 U/g (wet), available from Rö hm-Pharma) was added and the total volume of the reaction mixture was made up to 200 ml with water after the pH value had been adjusted to 6.4. Representative samples of the reaction mixture including solid constituents (except for the enzyme) were taken at the times specified in Table 7 and analyzed by HPLC. The results obtained are reported in Table 7.

TABLE 7

| Time | Concentration (mmol/l) found by HPLC | | | |
|---|---|---|---|---|
| (hours) | D-HPGA | 7-ADCA | Cedrox | D-HPG |
| 0.07 | 622 | 183 | 10.2 | 11 |
| 0.53 | 583 | 156 | 35.1 | 49 |
| 1.05 | 542 | 146 | 40.0 | 95 |
| 1.88 | 468 | 144 | 48.2 | 162 |
| 2.50 | 412 | 137 | 52.1 | 202 |
| 3.40 | 310 | 130 | 56.2 | 263 |
| 4.20 | 258 | 122 | 57.4 | 309 |
| 5.15 | 180 | 106 | 60.7 | 382 |

Experiment B

Same conditions as in experiment A were employed, except that micronized 2-naphthol (40 mmol) was added to the reaction mixture at the beginning Of the experiment. Representative samples of the reaction mixture including solid constituents (except for the enzyme) were taken at the times indicated in Table 8 and analyzed by HPLC. The results obtained are reported in Table 8.

TABLE 8

| Time | Concentration (mmol/l) found by HPLC | | | |
|---|---|---|---|---|
| (hours) | D-HPGA | 7-ADCA | Cedrox | D-HPG |
| 0.12 | 614 | 162 | 13.5 | 5 |
| 0.77 | 601 | 141 | 35.2 | 18 |
| 1.58 | 593 | 130 | 41.6 | 41 |
| 2.33 | 586 | 125 | 49.7 | 69 |
| 3.23 | 512 | 120 | 52.7 | 93 |
| 4.80 | 435 | 106 | 58.5 | 140 |
| 6.05 | 380 | 100 | 64.7 | 185 |

The ratios between the amount of cedrox formed and the amount of D-HPG formed due to an undesired side reaction in Experiments A and B are summarized in Table 9. The figures indicate that the efficiency with which the acylating agent, D-HPGA, is utilized is strongly dependent on the reaction conditions.

TABLE 9

| Experiment A | | Experiment B | |
|---|---|---|---|
| Time | Cedrox formed | Time | Cedrox formed |
| (hours) | D-HPG formed | (hours) | D-HPG formed |
| 0.07 | 0.93 | 0.12 | 2.70 |
| 0.53 | 0.72 | 0.77 | 1.96 |
| 1.05 | 0.42 | 1.58 | 1.01 |
| 1.88 | 0.30 | 2.33 | 0.72 |
| 2.50 | 0.26 | 3.23 | 0.57 |
| 3.40 | 0.21 | 4.80 | 0.42 |
| 4.20 | 0.19 | 6.05 | 0.35 |
| 5.15 | 0.16 | | |

I claim:

1. A method of preparing a β-lactam antibiotic comprising enzymatic acylation of a 7-amino-8-oxo-5-thia-1-azabicyclo [4.2.0]oct-2-ene nucleus in water or in a mixture of water and one or more water-miscible organic solvents by enzymatic acylation with the acid or a derivative of the acid corresponding to the desired side chain, characterized in that naphthalene or a naphthalene derivative with the formula Naphthyl-R wherein Naphthyl- designates 1-naphthyl or 2-naphthyl and R is selected from the group consisting of hydrogen, halogen, hydroxy, nitro, cyano, branched or unbranched alkyl of 1 to 6 carbon atoms optionally substituted with cyano, branched or unbranched alkoxy of 1 to 6 carbon atoms and alkanoyl of 1 to 6 carbon atoms, where on a molar basis the ratio between the amount of naphthalene or naphthalene derivative present in the reaction mixture and the amount of β-lactam antibiotic present in the reaction mixture is at least 0.45, is present in the reaction mixture during the formation of a naphthalene complex of the β-lactam antibiotic which is isolated or decomposed to the β-lactam antibiotic by deprotection of a protected intermediate.

2. A method according to claim 1, characterized in that in the reaction mixture part of the naphthalene or naphthalene derivative is in solid form.

3. A method according to claim 1, characterized in that the β-lactam antibiotic nucleus is selected from the group consisting of 7-aminocephalosporanic acid, 7-amino-7-methoxycephalosporanic acid, 7-amino-3-methoxy-3-cephem-4-carboxylic acid, 7-aminodesacetoxycephalosporanic acid, 3-chloro-7-amino-3-cephem-4-carboxylic acid, 7-amino-3-(1,2,3-triazol-4(5)-ylthiomethyl-3-cephem-4-carboxylic acid and 7-amino-3-[2-(5-methyl-1,3,4-thiadiazolyl)thiomethyl]-3-cephem-4-carboxylic acid.

4. A method according to claim 1, characterized in that the acylating agent used to introduce the β-lactam antibiotic side chain is D-phenylglycine or D-4-hydroxyphenylglycine or the amide, the methyl ester, the ethyl ester, the propyl ester or the isopropyl ester of one of these acids.

5. A method according to claim 1, characterized in that the enzyme used is classified as a penicillin acylase or as an ampicillin hydrolase.

6. A method according to claim 1, characterized in that enzyme from *Escherichia coli, Acetobacter pasteurianus, Xanthomonas citrii, Kluyvera citrophila, Bacillus megaterium* or *Pseudomonas melanogenum* is used.

7. A method according to claim 1, characterized in that enzyme used is immobilized.

8. A method according to claim 7, characterized in that the particles carrying the immobilized enzyme are separated from the remainder of the reaction mixture which comprises the particulate solid complex between the β-lactam antibiotic formed and naphthalene or a naphthalene derivative and optionally one or more other particulate solid component(s) and a liquid by giving the β-lactam antibiotic complex and the other particulate solid component(s), if any, a particle size which is different from the size of the particles carrying the enzyme and filtering or centrifuging the reaction mixture using equipment which will retain the component having the larger particles, be it the particles carrying the immobilized enzyme or the other solid component(s), and let the remainder of the mixture pass through.

9. A method according to claim 1, characterized in that during the formation of the cephalosporin the pH value in the reaction mixture is kept in the range from about 2.5 to about 9 with the proviso that when the cephalosporin is prepared by in situ acylation of a cephalosporin nucleus with the free side chain acid as the acylating agent then the pH value is preferably in the range from about 4 to about 9.

10. A method according to claim 1, characterized in that the naphthalene derivative used is 2-naphthol.

11. A method according to claim 9, characterized in that the pH value in the reaction mixture is held between about 4 to about 7.5 during the formation of the cephalosporin.

\* \* \* \* \*